United States Patent
Tsuji et al.

(10) Patent No.: US 7,705,166 B2
(45) Date of Patent: Apr. 27, 2010

(54) PROCESS FOR PRODUCING PROPYLENE OXIDE

(75) Inventors: Junpei Tsuji, Chiba (JP); Yoshiaki Itou, Ichihara (JP)

(73) Assignee: Sumitomo Chemical Company, Limited, Chuo-ku, Tokyo (JP)

( * ) Notice: Subject to any disclaimer, the term of this patent is extended or adjusted under 35 U.S.C. 154(b) by 979 days.

(21) Appl. No.: 10/572,878

(22) PCT Filed: Sep. 16, 2004

(86) PCT No.: PCT/JP2004/013998

§ 371 (c)(1),
(2), (4) Date: Mar. 22, 2006

(87) PCT Pub. No.: WO2005/030744

PCT Pub. Date: Apr. 7, 2005

(65) Prior Publication Data

US 2006/0281935 A1    Dec. 14, 2006

(30) Foreign Application Priority Data

Sep. 26, 2003   (JP) .............................. 2003-335326

(51) Int. Cl.
*C07D 301/19* (2006.01)
(52) U.S. Cl. ...................................................... 549/529
(58) Field of Classification Search .................. 549/529
See application file for complete search history.

(56) References Cited

U.S. PATENT DOCUMENTS

| | | | |
|---|---|---|---|
| 5,245,090 | A | 9/1993 | DeCaria et al. |
| 2003/0032822 | A1 | 2/2003 | Tsuji et al. |

FOREIGN PATENT DOCUMENTS

| | | |
|---|---|---|
| CZ | 140743 | 3/1971 |
| JP | 6-192151 A | 7/1994 |
| JP | 2001-270877 A | 10/2001 |
| JP | 2001-270880 A1 | 10/2001 |
| JP | 2003-160522 A | 6/2003 |

*Primary Examiner*—Bernard Dentz
(74) *Attorney, Agent, or Firm*—Sughrue Mion, PLLC

(57) ABSTRACT

A process for producing propylene oxide, which comprises the following steps:
  oxidation step: a step of obtaining cumene hydroperoxide by oxidizing cumene;
  epoxidation step: a step of obtaining propylene oxide and cumyl alcohol by reacting cumene hydroperoxide obtained in the oxidation step with propylene; and
  conversion step: a step of obtaining cumene by subjecting cumyl alcohol obtained in the epoxidation step to hydrogenation-containing reaction and recycling the cumene to the oxidation step,
  wherein a concentration of 1,2-epoxy-2-phenylpropane contained in the reaction mixture after the oxidation step, is 1% by weight or less.

3 Claims, No Drawings

PROCESS FOR PRODUCING PROPYLENE OXIDE

TECHNICAL FIELD

The present invention relates to a process for producing propylene oxide.

BACKGROUND ART

A process in which propylene is converted into propylene oxide using cumene hydroperoxide obtained from cumene as an oxygen carrier, cumyl alcohol produced together with propylene oxide is subjected to hydrogenolysis to obtain cumene and this cumene is used repeatedly, is disclosed in Czechoslovakia patent CS140743 and JP2001-270880 A. Though these processes are composed of the oxidation step, epoxidation step and hydrogenolysis step, it is difficult to say that they are necessarily sufficient in industrial efficiency.

DISCLOSURE OF THE INVENTION

An object of the invention is to provide a process for efficiently producing propylene having excellent characteristics in which propylene is converted into propylene oxide using cumene hydroperoxide obtained from cumene as an oxygen carrier, the cumene can be used repeatedly, and further oxidation can be carried out efficiency thereby being able to efficiently produce propylene oxide.

Namely, the present invention relates to a process for producing propylene oxide, which comprises the following steps:

oxidation step: a step of obtaining cumene hydroperoxide by oxidizing cumene;

epoxidation step: a step of obtaining propylene oxide and cumyl alcohol by reacting cumene hydroperoxide obtained in the oxidation step with propylene in the presence of an epoxidation catalyst; and conversion step: a step of converting cumyl alcohol obtained in the epoxidation step into cumene and recycling said cumene to the oxidation step, wherein a concentration of 1,2-epoxy-2-phenylpropane contained in a reaction mixture after the oxidation step is 1% by weight or less.

BEST MODE FOR CARRYING OUT THE INVENTION

The oxidation step is a step for obtaining cumene hydroperoxide by oxidizing cumene. The oxidation of cumene is usually conducted by auto-oxidation using an oxygen-containing gas such as air or oxygen-concentrated air. This oxidation may be conducted without use of an additive, and an additive such as an alkali may be used. The reaction temperature is usually from 50 to 200° C., and the reaction pressure is usually between atmospheric pressure and 5 MPa. In the oxidation method in which the additive is used, an alkali metal compound such as NaOH or KOH, an alkaline earth metal compound, or alkali metal carbonate such as $Na_2CO_3$ or $NaHCO_3$, ammonia, $(NH_4)_2CO_3$, an alkali metal ammonium carbonate or the like, is used as an alkali reagent.

The epoxidation step is a step for obtaining propylene oxide and cumyl alcohol by reacting cumene hydroperoxide obtained in the oxidation step with propylene. The epoxidation step is preferably conducted in the presence of an epoxidation catalyst, particularly a catalyst containing titanium-containing silicon oxide from the viewpoint of obtaining the object compound under high yield and high selectivity. As the catalyst, so-called Ti-silica catalysts containing Ti chemically bonded to silicon oxide, are preferable. For example, a catalyst prepared by supporting a Ti compound on a silica carrier, a catalyst prepared by combining a Ti compound with silicon oxide by a co-precipitation method or sol gel method, zeolite compounds containing Ti, and the like, can be listed. Cumene hydroperoxide used as a raw material in the epoxidation step, may be a dilute or dense purified material or non-purified material.

The epoxidation is conducted by contacting propylene and cumene hydroperoxide with the catalyst. The reaction is carried out in a liquid phase using a solvent. The solvent should be liquid under a temperature and a pressure during the reaction, and substantially inert to reactants and products. The solvent may be a substance present in a hydroperoxide solution to be used. For example, when cumene hydroperoxide is a mixture with cumene which is a raw material thereof, the cumene can be used as a substitute of a solvent without particularly adding a solvent.

The epoxidation temperature is usually from 0 to 200° C., and preferably from 25 to 200° C. The pressure may be a pressure sufficient to keep the reaction mixture in a liquid condition. In general, the pressure is advantageously from 100 to 10,000 kPa.

The solid catalyst can be advantageously used in the form of a slurry or fixed bed. In the case of a large-scale industrial operation, a fixed bed is preferably used. In addition, the epoxidation can be conducted by a batch-wise method, a semi-continuous method or a continuous method.

When a liquid containing a raw material for reaction is passed through a fixed bed, the catalyst is not contained at all or substantially in a liquid mixture drawn out from the reaction zone.

The conversion step is a step for obtaining cumene by subjecting cumyl alcohol obtained in the epoxidation step to hydrogenation-containing reaction and recycling the cumene to the oxidation step. As a method for converting cumyl alcohol into cumene, a method of first dehydrating cumyl alcohol to obtain α-methylstyrene and then hydrogenating α-methylstyrene to convert into cumene (dehydration-hydrogenation method), and a method of subjecting cumyl alcohol to hydrogenolysis to directly convert into cumene, can be illustrated.

A case in which the conversion step is composed of the dehydration step and hydrogenation step, is explained below.

It is preferable to separate propylene oxide obtained by the epoxidation from cumyl alcohol before the dehydration step from the viewpoint of obtaining high yield of propylene oxide.

As a separation method, distillation can be used.

A catalyst used in the dehydration includes acids such as sulfuric acid, phosphoric acid and p-toluene sulfonic acid and metal oxides such as activated alumina, titania, zirconia, silica-alumina and zeolites, and activated alumina is preferable from viewpoints of separation from the reaction mixture, catalyst life, selectivity, etc.

The dehydration is usually conducted by contacting cumyl alcohol with the catalyst, but, in the present invention, hydrogen may be fed together with cumyl alcohol to the catalyst to conduct hydrogenation subsequent to the dehydration. The reaction can be conducted in a liquid phase using a solvent. The solvent should be substantially inert to reactants and products. The solvent may be a substance present in a cumyl alcohol solution to be used. For example, when cumyl alcohol is a mixture with cumene as a product, it is possible to use cumene as a substitute without adding a solvent in particular.

The dehydration temperature is usually 50 to 450° C., preferably 150 to 300° C. In usual, the pressure is advantageously 10 to 10,000 kPa. The dehydration can be advantageously conducted by using a catalyst in a slurry form or fixed-bed form.

The hydrogenation step is a step for converting into cumene by supplying α-methylstyrene obtained by the dehydration to a hydrogenation catalyst to hydrogenate a-methylstyrene and for recycling cumene to the oxidation step as a raw material in the oxidation step.

Though the hydrogenation catalyst includes catalysts containing a metal of Group 10 or 11 of the Periodic Table, and specifically, nickel, palladium, platinum and copper, palladium or copper are preferable from viewpoints of suppression of hydrogenation of the aromatic ring and high yield. As a copper catalyst, copper, Raney copper, copper/chromium, copper/zinc, copper/chromium/zinc, copper/silica, copper/alumina and the like are listed. As a palladium catalyst, palladium/alumina, palladium/silica, palladium/carbon and the like are listed. These catalysts can be used alone or in combination of two or more.

Though the hydrogenation is usually carried out by contacting α-methylstyrene and hydrogen with the catalyst, a part or the whole of water generated may be separated by oil-water separation or the like or may be supplied together with α-methylstyrene to the hydrogenation catalyst for carrying out the hydrogenation subsequent to the dehydration.

Though the amount of hydrogen required in the reaction may be equimolar to α-methylstyrene theoretically, an excess amount of hydrogen is required because other components which consume hydrogen are contained in the raw material.

As a molar ratio of hydrogen to α-methylstyrene, the range of 1 to 10 is usually applied because the reaction proceeds rapidly with increase of a partial pressure of hydrogen. The range is further preferably 1 to 5. The excess amount of hydrogen remained after the reaction can be recycled after separated from the reaction mixture. The hydrogenation can be conducted in a liquid phase using a solvent or gas phase. The solvent must be substantially inert to the reactants and products. The solvent may be a substance existing in an α-methylstyrene solution to be used. For example, when α-methylstyrene is a mixture with cumene as a product, it is possible to use cumene as a substitute of the solvent without adding a solvent in particular. The hydrogenation temperature is usually 0 to 500° C., preferably 30 to 400° C. In usual, the pressure is advantageously 100 to 10,000 kPa.

As modes of the dehydration and hydrogenation, these reactions can be advantageously conducted by a continuous method using a catalyst in the form of a fix-bed. The dehydration and hydrogenation may be conducted using separate reactors or a single reactor. As a reactor used in the continuous method, there are an adiabatic reactor and an isothermal reactor, and the adiabatic reactor is preferable because the isothermal reactor requires an apparatus for removal of heat. In a case of a single adiabatic reactor, the temperature lowers with progress of the reaction because the dehydration of cumyl alcohol is an endothermic reaction, and on the other hand, since the hydrogenation of α-methylstyrene is an exothermic reaction, the temperature rises with progress of the reaction. The outlet temperature becomes higher than the inlet temperature because the generated heat quantity is larger in total.

The reaction temperature and pressure are selected so that water contained in an α-methylstyrene solution after the dehydration, is not condensed. The reaction temperature is preferably 150 to 300° C., and the reaction pressure is preferably 100 to 2000 kPa. When the temperature is too low or the pressure is too high, water may be condensed at the outlet of the dehydration, leading to deterioration of the performance of the hydrogenation catalyst. Further, when the pressure is too high, it is also disadvantageous in the reaction equilibrium of dehydration. When the temperature is too high or the pressure is too low, it may become disadvantageous because the catalyst life is shortened by howling or the like caused by much generation of the gas phase part.

Though hydrogen can be supplied from any one of an inlet of a dehydration reactor and an inlet of a hydrogenation reactor, it is preferable to supply from the inlet of the dehydration reactor in view of the activity of the dehydration catalyst. That is, vaporization of water produced through dehydration is promoted by bringing into constant existence of hydrogen in the dehydration zone and the equilibrium dehydration conversion rises, therefore, high conversion can be attained effectively compared to absence of hydrogen. Though water generated in the dehydration is passed through the hydrogenation catalyst, it is possible to operate at low cost without particularly setting up an apparatus for water removal as described above, by operating at the level not condensing water. Further, unreacted hydrogen in the outlet of the reactor can be recycled after gas-liquid separation operation.

Furthermore, at the time of the gas-liquid separation operation, it is possible to separate water generated in the dehydration from the reaction mixture. A part of the obtained reaction mixture (mainly cumene) can be recycled to the inlet of the reactor for use.

An amount of the dehydration catalyst used may be an amount enough to convert cumyl alcohol, and the conversion of cumyl alcohol is preferably 90% or more. An amount of the hydrogenation catalyst used may be an amount enough to convert α-methylstyrene, and the conversion of α-methylstyrene is preferably 98% or more.

Considering from a viewpoint of cost, the dehydration and hydrogenation catalysts are preferably packed in single fixed bed reactor but not in multi stage reactors. Inside of the reactor may be partitioned into several beds or not. When the reactor is not partitioned, the dehydration catalyst and hydrogenation catalyst may be directly contacted each other or those may be partitioned with an inert packing.

A case of which production of cumene from cumyl alcohol is conducted by hydrogenolysis, is explained below:

The hydrogenolysis step is a step for obtaining cumene by subjecting cumyl alcohol obtained in the epoxidation step to hydrogenolysis and for recycling the cumene as a raw material to the oxidation step. In other words, cumene which has been used in the oxidation step is reproduced by the hydrogenolysis. The hydrogenolysis is carried out by contacting cumyl alcohol and hydrogen with a catalyst. As the catalyst, any catalyst having hydrogenation ability can be used. Though examples of the catalyst include metal-based catalysts of metals of Groups 8 to 10 such as cobalt, nickel and palladium metal and metal-based catalysts of metals of Groups 11 and 12 such as copper and zinc, copper-based catalysts are preferable from the viewpoint of suppression of by-products.

As the copper-based catalyst, copper, Raney copper, copper-chromium, copper-zinc, copper-chromium-zinc, copper-silica, copper-alumina and the like are listed.

The reaction can be conducted in a liquid phase using a solvent or a gas phase. The solvent should be substantially inert to the reactants and products. The solvent may be a substance existing in a cumyl alcohol solution to be used. For example, when cumyl alcohol is a mixture with cumene as a product, it is possible to use cumene as a substitute of the solvent without adding a solvent in particular.

Though the amount of hydrogen required in the hydrolysis may be equimolar to cumyl alcohol, an excess amount of hydrogen is required because other components which consume hydrogen, are contained in the raw material. Further, the molar ratio of hydrogen to cumyl alcohol is usually from 1 to 10 because the reaction proceeds rapidly with increase of a partial pressure of hydrogen. The ratio is further preferably from 1 to 5. The excess amount of hydrogen remained after the reaction may be recycled after separated from the reaction mixture. The hydrogenolysis temperature is usually 0 to 500° C., preferably 30 to 400° C. In usual, the pressure is advantageously 100 to 10,000 kPa. The hydrolysis can be advantageously carried out using a catalyst in the form of slurry or a fixed bed.

The present process can be conducted by a batch method, semi-continuous method or continuous method.

When a liquid or gas containing a raw material for reaction is passed through a fixed bed, the catalyst is not contained at all or substantially in a liquid mixture drawn out from the reaction zone.

In the present invention, it is required that a concentration of 1,2-epoxy-2-phenylpropane contained in the reaction mixture after the oxidation step is 1% by weight or less, and 0.5% by weight or less is preferred.

When the concentration of 1,2-epoxy-2-phenylpropane contained in the reaction mixture after the oxidation step is over 1% by weight, a reaction yield in the oxidation step deteriorates because amounts of cumyl alcohol and acetophenone formed increase. Though cumyl alcohol can be returned to cumene via the hydrogenation step, it is not preferred economically as a process of propylene oxide production because hydrogen of equimolar to cumyl alcohol, is consumed. In addition, acetophenone is a compound in which the carbon number was reduced, therefore, it converts into ethylbenzene via the conversion step, leading to a loss of cumene.

Though distillation removal, removal through reaction, adsorption removal and the like are listed as methods for controlling the 1,2-epoxy-2-phenylpropane concentration to the range within the present invention, it is preferable as a method of controlling generation of 1,2-epoxy-2-phenylpropane to optimize the reaction conditions of oxidation such as temperature and time or to reduce alcohols and olefins other than cumene as much as possible.

EXAMPLE

Example 1

Cumene recycled from a hydrogenation step was mixed with an aqueous solution of 1.5 wt.% of sodium carbonate in a weight ratio of 1 of the aqueous solution to 20 of cumene, and the mixture was reacted under a pressure of 630 kPa and a temperature of 90 to 105° C. for 5 hours supplying air.

At this time, a concentration of 1,2-epoxy-2-phenylpropane was 0.2% by weight. A formed oxidized liquid had the following composition.

| | |
|---|---|
| Cumene hydroperoxide | 14.6% by weight |
| Cumyl alcohol | 0.1% by weight |
| Cumene | 83.9% by weight |
| Acetophenone | 0.1% by weight |

Example 2

A reaction operation was carried out in the same manner as in Example 1 except that the amount of cumene recycled from the hydrogenation step, was changed.

At this time, a concentration of 1,2-epoxy-2-phenylpropane was 0.6% by weight. A formed oxidized liquid had the following composition.

| | |
|---|---|
| Cumene hydroperoxide | 24.4% by weight |
| Cumyl alcohol | 1.3% by weight |
| Cumene | 72.6% by weight |
| Acetophenone | 0.4% by weight |

Comparative Example 1

A reaction operation was carried out in the same manner as in Example 1 except that the amount of cumene recycled from the hydrogenation step, was changed.

At this time, a concentration of 1,2-epoxy-2-phenylpropane was 1.5% by weight. A formed oxidized liquid had the following composition.

| | |
|---|---|
| Cumene hydroperoxide | 25.4% by weight |
| Cumyl alcohol | 2.0% by weight |
| Cumene | 68.8% by weight |
| Acetophenone | 0.7% by weight |

INDUSTRIAL APPLICABILITY

According to the present invention, there could be provided a process for producing propylene oxide, which can convert propylene into propylene oxide using cumene hydroperoxide obtained from cumene as an oxygen carrier, use repeatedly the cumene and further efficiently carry out oxidation thereby being able to efficiently produce propylene oxide.

The invention claimed is:

1. A process for producing propylene oxide, which comprises the following steps:
    oxidation step: a step of obtaining cumene hydroperoxide by oxidizing cumene;
    epoxidation step: a step of obtaining propylene oxide and cumyl alcohol by reacting cumene hydroperoxide obtained in the oxidation step with propylene; and
    conversion step: a step of obtaining cumene by subjecting cumyl alcohol obtained in the epoxidation step to hydrogenation-containing reaction and recycling the cumene to the oxidation step,
    wherein a concentration of 1,2-epoxy-2-phenylpropane contained in a reaction mixture after the oxidation step is 1% by weight or less.

2. The process according to claim 1, wherein the conversion step comprises the following steps:
    dehydration step: a step of obtaining α-methylstyrene by dehydrating cumyl alcohol obtained in the epoxidation step in the presence of a dehydration catalyst; and
    hydrogenation step: a step of obtaining cumene by hydrogenating α-methylstyrene in the presence of a hydrogenation catalyst to obtain cumene, and recycling the cumene to the oxidation step.

3. The process according to claim 1, wherein the conversion step comprises the following step:
    hydrogenolysis step; a step of obtaining cumene by subjecting cumyl alcohol obtained in the epoxidation step to hydrogenolysis in the presence of a hydrogenolysis catalyst, and recycling the cumene to the oxidation step as the raw material.

* * * * *